United States Patent [19]

Murakami

[11] Patent Number: 5,216,151
[45] Date of Patent: Jun. 1, 1993

[54] PROCESS FOR PRODUCING BENZYLPHTHALAZINONE DERIVATIVES AND SALTS THEREOF

[75] Inventor: Kazukata Murakami, Ibaraki Prefecture, Japan

[73] Assignee: Eisai Chemical Co., Ltd., Kashima, Japan

[21] Appl. No.: 800,259

[22] Filed: Nov. 29, 1991

[30] Foreign Application Priority Data

Nov. 28, 1990 [JP] Japan .................. 2-322399

[51] Int. Cl.$^5$ .................. C07D 403/14; C07D 403/04
[52] U.S. Cl. .................. 540/599; 544/235; 544/237
[58] Field of Search .................. 540/599; 544/235, 237

[56] References Cited

U.S. PATENT DOCUMENTS

| | | | |
|---|---|---|---|
| 3,813,384 | 5/1974 | Vogelsang et al. | 540/599 |
| 4,841,047 | 6/1989 | Engel et al. | 540/599 |
| 4,868,175 | 9/1989 | Engel et al. | 540/599 |
| 4,939,140 | 7/1990 | Larson et al. | 544/237 |

FOREIGN PATENT DOCUMENTS

| | | | |
|---|---|---|---|
| 174464 | 3/1986 | European Pat. Off. | 540/599 |
| 289939 | 11/1988 | European Pat. Off. | 540/599 |
| 316639 | 5/1989 | European Pat. Off. | 540/599 |
| 396069 | 11/1990 | European Pat. Off. | 540/599 |

OTHER PUBLICATIONS

Wada et al;, Tetrahedron Lett. No. 13, pp. 1279-1282, (1972).
Grynkiewcz, CA86-140400f (1977).
Ozaki et al. CA 85-108941b (1976).

*Primary Examiner*—Cecilia Tsang
*Attorney, Agent, or Firm*—Wenderoth, Lind & Ponack

[57] ABSTRACT

A process for producing benzylphthalazinone derivatives represented by the general formula (I);

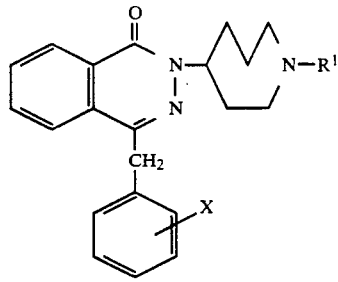

[I]

wherein X is a halogen atom and $R^1$ is a lower alkyl group, and salts thereof, which comprises reacting a compound represented by the general formula (II);

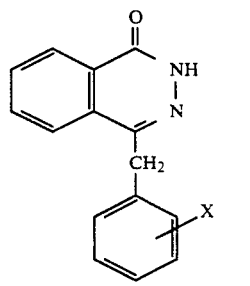

[II]

wherein X has the same meaning as mentioned above, or a salt thereof with a compound represented by the general formula (III);

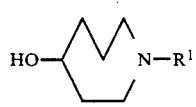

[III]

wherein $R^1$ has the same meaning as mentioned above or salt thereof in the presence of a dehydration-condensation agent. The benzylphthalazinone derivatives thereof are suitable for use as an antihistaminic agent.

6 Claims, No Drawings

PROCESS FOR PRODUCING BENZYLPHTHALAZINONE DERIVATIVES AND SALTS THEREOF

BACKGROUND OF THE INVENTION

1. Field of the Invention

This invention relates to an improved process for producing benzylphthalazinone derivatives with a high yield.

2. Description of the Prior Art

Japanese Patent Publication No. 31154/1980 describes that the compound represented by the general formula [I];

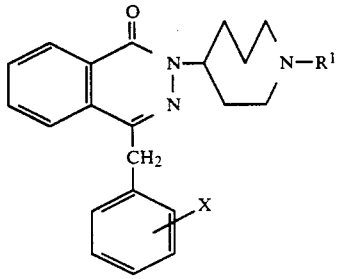

wherein X is a halogen atom and $R^1$ is a lower alkyl group, is suitable for use as an antihistaminic agent and discloses a process for preparing said compound utilizing the cyclic ammonium transition method. According to this conventional art, a crude final product can be obtained at an yield of at least 90%, which however contains a large quantity of by-products. If the target product is isolated from the crude product by crystallization, the yield will fall to 30% or lower.

For the reasons stated above, this conventional art is not satisfactory for commercial production.

Thus, there is a definite need in the art for a process for producing benzylphthalazinone derivatives (so-called "benzylphthalazone derivatives") with a high yield.

There is also a need in the art for a process for producing benzylphthalazinone derivatives with a high yield which does not require severe reaction conditions.

A BRIEF SUMMARY OF THE INVENTION

Accordingly, an object of this invention is to provide a process for producing benzylphthalazinone derivatives with a high yield.

Another object of this invention is to provide a process for producing benzylphthalazinone derivatives with a high yield which does not require severe reaction conditions.

A further object of this invention is to provide a process for producing benzylphthalazinone derivatives employing dehydration-condensation agent and unique control of reaction temperature.

DETAILED DESCRIPTION OF THE INVENTION

As previously described, the conventional art is not satisfactory because the product yield is rather low. As a result of devoted study, the present inventor has established an improved process for producing benzylphthalazinone derivatives with a high yield.

According to this invention, a process is presented for producing benzylphthalazinone derivatives represented by the general formula [I]:

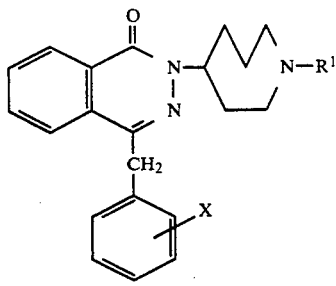

wherein X is a halogen atom and $R^1$ is a lower alkyl group, or salts thereof, which comprises reacting a compound represented by the general formula [II]:

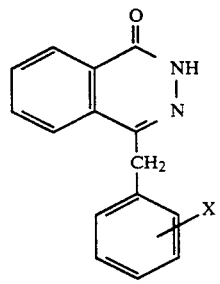

wherein X has the same meaning as mentioned above, or a salt thereof with a compound represented by the general formula [III]:

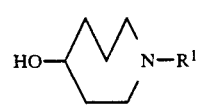

wherein $R^1$ has the same meaning as mentioned above, or a salt thereof, in the presence of a dehydration-condensation agent.

Illustrative of the halogen atom of X in the general formula [I] include Cl, Br and I, and exemplary lower alkyl groups of $R^1$ include methyl, ethyl, propyl and the like.

Examples of the salt of the compound represented by the general formula [I] include acid addition salts such as inorganic acid salts, for example, hydrochloride, sulfate, carbonate, bicarbonate, hydrobromate and hydroiodate; organic carbonates, for example, acetate, maleate, fumarate, lactate, and tartrate; and organic sulfonates, for example, methanesulfonate, benzenesulfonate and toluenesulfonate.

As the salt of the compound represented by the general formula [III], there can be given salts similar to those exemplified above as the salt of the compound represented by the general formula [I]. In addition, as the salt of the compound represented by the general formula [II], there can be mentioned alkali metal salts such as sodium salts and potassium salts as well as the acid addition salts exemplified in the compound of the general formula [I].

As a dehydration-condensation agent, there can be used a combination of an azodicarboxylate represented by the general formula [IV]:

   [IV]

wherein $R^2$ represents a lower alkyl group, with a compound selected from the group consisting of phosphine derivatives represented by the general formula:

$(R^3)_3P$ wherein $R^3$ represents an aryl group or a lower alkyl group; a lower alkylamine, and an N-lower alkyl-substituted piperazine.

Examples of the lower alkyl group of $R^2$ include methyl, ethyl and isopropyl group. Illustrative of the aryl group of $R^3$ include phenyl group and that of the lower alkyl group of $R^3$ include an n-butyl group. Moreover, exemplary lower alkyl amines include dimethylamine and diethylamine and exemplary N-lower alkyl substituted piperazines include N-methylpiperazine and N-ethylpiperazine. The most preferred dehydration-condensation agent may be a combination of diethyl azodicarboxylate with triphenylphosphine or a combination of diisopropyl azodicarboxylate with triphenylphosphine.

The means whereby this invention may be practiced can be varied widely. The amount of the starting materials used in the reaction of this invention is not narrowly critical, the molar ratio of the compound represented by the general formula (II) to the compound represented by the general formula (III) can range from about 1:1 or less to about 0.5:1 or greater. Preferably from about 1:1 to about 0.8:1 may be employed without departing from the scope of the invention.

The reaction temperature at which the reaction of this invention may be conducted is not narrowly critical and can range from about $-80°$ C. to about $100°$ C., although it is desirable to conduct the reaction at temperature of $-20°$ C. or lower to avoid the formation of undesired by-products.

The reaction of this invention may be conducted at atmospheric pressure, although higher or lower pressure may also be used depending upon the other conditions of reaction, the ingredients used, the speed at which it is desired to effect reaction, etc.

The reaction of this invention may be conducted in an inert solvent.

Any solvent can be used as long as it should be inert under the reaction conditions, and of such a nature that separation from the target product will not be difficult. Even the solvent in which the reaction materials are not dissolved completely can be also used.

Examples of useful solvents that meet the foregoing qualifications include aromatic hydrocarbons such as benzene, mesitylene, toluene, xylene and the like; heterocyclic compounds such as pyridine and the like; ethers such as diethyl ether, tetrahydrofuran, dioxane, diisopropyl ether and the like; sulfoxides such as dimethyl sulfoxide and the like; amides such as dimethylacetamide, hexamethylphosphoric triamide, tetramethylurea and the like, N-methylpyrrolidone and the like. These solvents may be ued either singley or in combination.

The amount of an inert solvent used in the reaction of this invention is not narrowly critical and can range from about 5 weight percent or less to about 30 weight percent or greater of the total weight of the starting materials.

The target product produced by the process of this invention can be isolated by crystallization. For example, a crude reaction product can be concentrated under atmospheric or reduced pressure to obtain a concentrate, and then is added a lower alcohol such as methanol, ethanol, isopropanol, amyl alcohol, butanol or t-butanol, or acetone to the concentrate and dissolved. To the resulting solution, a strong inorganic acid or organic acid is added, whereby the target product is precipitated as crystals. Particularly preferred acids used in the crystalization include but are not limited to, for instance, hydrohalogenic acids such as hydrochloric acid, hydrobroic acid and hydroiodic acid.

The benzylphthalazinone derivatives and salts thereof produced by this invention are suitable for use as an antihistaminic agent.

In order that those skilled in the art may better understand how this invention may be practiced, the following examples are given by way of illustration and not by way of limitation.

EXAMPLE 1

Preparation of 4-(p-chlorobenzyl)-2-[N-methylperhydroazepinyl-(4)]-1-(2H)-phthalazinone hydrochloride represented by the formula

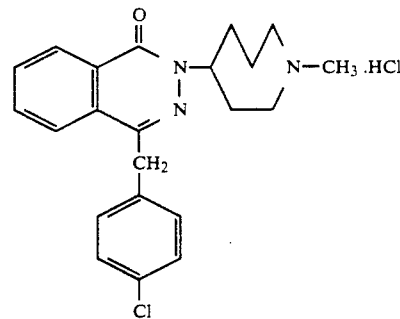

After 236.1 g of triphenyl phosphine were dissolved in 1 l of tetrahydrofuran, the solution was cooled to $-30°$ C. To the thus-cooled solution, 156.8 g of diethyl azodicarboxylate were added dropwise. Then, 81.2 g of 4-(p-chlorobenzyl)-1-(2H)-phthalazinone were added to the solution, followed by the dropwise addition of 100 ml of a tetrahydrofuran solution containing 38.9 g of N-methyl-4-homopiperizinol dissolved therein. The resultant solution was stirred for 16 hours while being maintained at $-30°$ C. After an additional 5-hour stirring at $20°$ C., the reaction mixture was concentrated at $50°$ C. under reduced pressure. The residue was dissolved in 1 l of isopropyl alcohol, followed by the addition of a concentrated hydrochloric acid. The crystals thus precipitated were subjected to suction filtration, washed with isopropyl alcohol and dried to obtain 106.7 g of the title product as white powdery crystals (yield: 85%).

Melting point: $225°$ C.

Mass spectrum (m/e): 381 (M+)

| Elemental analysis data: | C | H | N |
|---|---|---|---|
| Calculated (%) | 63.16 | 6.02 | 10.04 |

| -continued | | | |
|---|---|---|---|
| Elemental analysis data: | C | H | N |
| Found (%) | 63.05 | 6.07 | 10.08 |

Infrared absorption spectrum (cm$^{-1}$, Nujol): 3050, 2930, 1655, 1590, 1490, 690

$^1$H-NMR spectrum (δ, D$_2$O): 2.1–2.4 (b, 6H), 2.9 (s, 3H), 3.3–3.6 (b, 4H), 4.6 (s, 2H), 5.4 (m, 1H), 7.5 (m, 4H), 8.1 (m, 3H), 8.5 (m, 1H)

EXAMPLE 2

Preparation of 4-(p-chlorobenzyl)-2-[N-methylperhydroazepinyl-(4)]-1-(2H)-phthalazinone hydrochloride represented by the formula

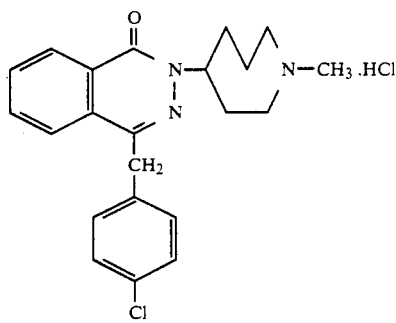

After 23.6 g of triphenyl phosphine were dissolved in 200 ml of tetrahydrofuran, the solution was cooled to −30° C. To the thus-cooled solution, 15.7 g of diethyl azodicarboxylate were added dropwise. Then, 8.1 g of 4-(p-chlorobenzyl)-1-(2H)-phthalazinone were added to the solution without changing the temperature, followed by the dropwise addition of 10 ml of a tetrahydrofuran solution containing 3.9 g of N-methyl-4-homopiperizinol dissolved therein. The resultant solution was stirred for 16 hours while being maintained at −30° C. After an additional 5-hour stirring at 20° C., 4.8 g of a concentrated hydrochloric acid were added to the reaction mixture. Then, the resultant mixture was added with 400 ml of acetone, filtered and dried to obtain 10.7 g of the title product as white powdery crystals (yield: 85%).

The crystals thus obtained had the same physical values as those of the crystals obtained in Example 1.

EXAMPLE 3

Preparation of 4-(p-chlorobenzyl)-2-[N-methylperhydroazepinyl-(4)]-1-(2H)-phthalazinone hydrochloride represented by the formula

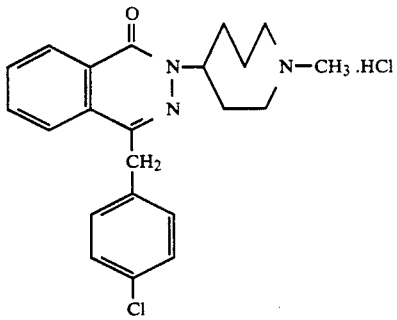

After 118.0 g of triphenyl phosphine were dissolved in 500 ml of tetrahydrofuran, the solution was cooled to −30° C. To the solution, 91.0 g of diisopropyl azodicarboxylate were added dropwise. Then, 40.5 g of 4-(p-chlorobenzyl)-1-(2H)-phthalazinone were added to the solution without changing the temperature, followed by the dropwise addition of 50 ml of a tetrahydrofuran solution containing 19.5 g of N-methyl-4-homopiperizinol dissolved therein. The resultant solution was stirred for 16 hours at −30° C. After an additional 5-hour stirring at 20° C., 24 g of a concentrated hydrochloric acid were added to the reaction mixture. Then, the resultant mixture was added with 2 l of acetone, filtered and dried to obtain 53.5 g of the title product as white powdery crystals (yield: 85%).

The crystals thus obtained had the same physical values as those of the crystals obtained in Example 1.

EXAMPLE 4

Preparation of 4-(p-chlorobenzyl)-2-[N-methylperhydroazepinyl-(4)]-1-(2H)-phthalazinone hydrochloride represented by the formula

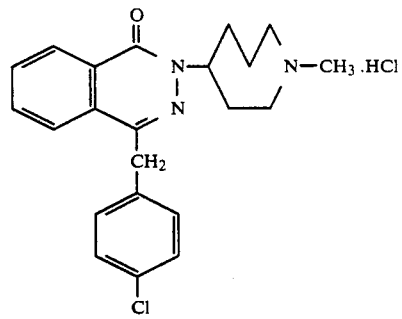

After 23.6 g of triphenyl phosphine were dissolved in 200 ml of tetrahydrofuran, the solution was cooled to −30° C. To the solution, 15.7 g of diethyl azodicarboxylate were added dropwise. Further, 8.1 g of 4-(p-chlorobenzyl)-1-(2H)-phthalazinone were added to the solution without changing the temperature, followed by the dropwise addition of 10 ml of a tetrahydrofuran solution containing 3.9 g of N-methyl-4-homopiperizinol dissolved therein. The resultant solution was stirred for 5 hours at −30° C., 5 hours at 0° C.

and 5 hours at 20° C., successively and was added with 4.8 g of a concentrated hydrochloric acid. Then, the resultant mixture was added with 400 ml of acetone, filtered and dried to obtain 10.7 g of the title product as white powdery crystals (yield: 85%).

The crystals thus obtained had the same physical values as those of the crystals obtained in Example 1.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for producing benzylphthalazinone derivatives represented by the following formula (I);

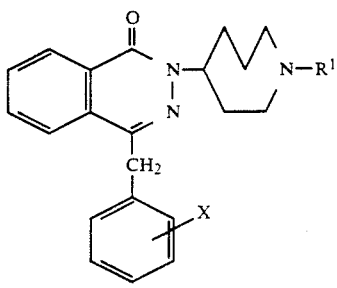

wherein X is a halogen atom and $R^1$ is a lower alkyl group, and salts thereof, which comprises reacting a compound represented by the following formula (II);

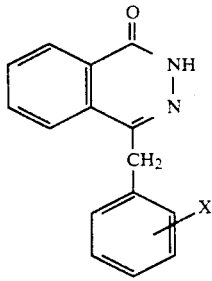

wherein X has the same meaning as mentioned above, or a salt thereof with a compound represented by the following formula (III);

 [III]

wherein $R^1$ has the same meaning as mentioned above, or a salt thereof, in the presence of a dehydration-condensation agent.

2. The process for producing benzylphthalazinone derivatives and salts thereof as claimed in claim 1, wherein X is chlorine atom and $R^1$ is methyl group.

3. The process for producing benzylphthalazinone derivatives and salts thereof as claimed in claim 1, wherein the dehydration-condensation agent is a combination of an azodicarboxylate represented by the following formula:

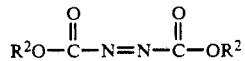

wherein $R^2$ is a lower alkyl group, with a compound selected from the group consisting of phosphine derivatives represented by the following formula:

$(R^3)_3P$ wherein $R^3$ represents an aryl group or a lower alkyl group.

4. The process for producing benzylphthalazinone derivatives and salts thereof as claimed in claim 3, wherein the dehydration-condensation agent is a combination of diethyl azodicarboxylate with triphenyl phosphine or a combination of diisopropyl azodicarboxylate with triphenyl phosphine.

5. The process for producing benzylphthalazinone derivatives and salts thereof as claimed in claim 1, wherein the salt is hydrochloride.

6. The process for producing benzylphthalazinone derivatives and salts thereof as claimed in claim 1, wherein the compound of the formula (II) is reacted with the compound of the formula (III) at a temperature in the range from −80° C. to 100° C.

* * * * *